US009279791B2

(12) United States Patent
Fukui et al.

(10) Patent No.: US 9,279,791 B2
(45) Date of Patent: Mar. 8, 2016

(54) ODOR SENSING SYSTEM

(71) Applicant: Empire Technology Development LLC, Wilmington, DE (US)

(72) Inventors: Toshimi Fukui, Otsu (JP); Junko Nakamoto, Osaka (JP)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/994,094

(22) PCT Filed: Nov. 26, 2012

(86) PCT No.: PCT/JP2012/007568
§ 371 (c)(1),
(2) Date: Jun. 13, 2013

(87) PCT Pub. No.: WO2014/080443
PCT Pub. Date: May 30, 2014

(65) Prior Publication Data
US 2015/0308993 A1    Oct. 29, 2015

(51) Int. Cl.
G01N 33/497 (2006.01)
G01N 30/86 (2006.01)
G01N 30/78 (2006.01)
(Continued)

(52) U.S. Cl.
CPC .......... *G01N 30/8675* (2013.01); *G01N 30/78* (2013.01); *G01N 33/0034* (2013.01); *G01N 33/00* (2013.01); *G01N 33/0001* (2013.01);
(Continued)

(58) Field of Classification Search
CPC .......... G01N 33/0001; G01N 33/0006; G01N 33/0009; G01N 33/0031; G01N 33/0004; G01N 33/0034; G01N 33/00
USPC .......... 73/23.34–23.36, 23.2, 24.06
See application file for complete search history.

(56) References Cited

U.S. PATENT DOCUMENTS 6,190,858 B1 *  2/2001  Persaud .................. C12Q 1/04
                                                 435/283.1
6,387,329 B1 *  5/2002  Lewis ................ G01N 15/0826
                                                 422/83

(Continued)

FOREIGN PATENT DOCUMENTS

EP    1 368 645    8/2011
JP    6-082431     3/1994
(Continued)

OTHER PUBLICATIONS

International Search Report and Written Opinion; International Application No. PCT/JP2012/007568, Filed on Nov. 26, 2012; mailed on Feb. 19, 2013; 6 pages.
(Continued)

*Primary Examiner* — Lisa Caputo
*Assistant Examiner* — Jonathan Dunlap
(74) *Attorney, Agent, or Firm* — Knobbe Martens Olson & Bear, LLP

(57) ABSTRACT

An odor sensing system including a plurality of odor sensors, each odor sensor being configured to output a detection signal in response to at least one odor molecule; at least one chromatographic membrane disposed at the plurality of odor sensors through which the odor molecule diffuses to reach the odor sensor; and a pattern analyzer configured to analyze the detection signals over time to identify the odor molecule is described.

33 Claims, 11 Drawing Sheets

(51) Int. Cl.
G01N 33/00 (2006.01)
G01N 30/52 (2006.01)

(52) U.S. Cl.
CPC ........ *G01N 33/0004* (2013.01); *G01N 33/0031* (2013.01); *G01N 2030/527* (2013.01)

(56) References Cited

U.S. PATENT DOCUMENTS

| | | | | |
|---|---|---|---|---|
| 6,703,241 | B1* | 3/2004 | Sunshine | G01N 33/0006 436/147 |
| 8,726,719 | B2* | 5/2014 | Vass | G01N 33/0031 73/23.2 |
| 8,880,448 | B2* | 11/2014 | Haddad | G01N 33/0034 510/103 |
| 2004/0161370 | A1* | 8/2004 | Sunshine | G01N 33/0006 422/83 |
| 2004/0244465 | A1* | 12/2004 | Bresciani | G01N 33/0009 73/23.34 |
| 2006/0191319 | A1* | 8/2006 | Kurup | G01N 33/24 73/23.34 |
| 2007/0184238 | A1* | 8/2007 | Hockaday | B32B 7/00 428/98 |

FOREIGN PATENT DOCUMENTS

| JP | 10-170422 | 6/1998 |
|---|---|---|
| JP | 2007-218704 | 8/2007 |
| JP | 2010-112909 | 5/2010 |

OTHER PUBLICATIONS

Tang, Kea-Tiong et al., "A Low-Power Electronic Nose Signal-Processing Chip for a Portable Artificial Olfaction System"; Biomedical Circuits and Systems, IEEE Xplore Digital Library; published Apr. 5, 2011, vol. 5, issue 4, 1 page.

Harun, F K Che, et al., "Portable e-mucosa system mimicking the biological olfactory . . . ", Procedia Chemistry (2009), vol. 1, Elsevier Science BV; 1 page.

http://www.s.u-tokyo.ac.jp/ja/press/2010/20.html, [retrieved from internet Mar. 14, 2013], 2 pages.

"Smelling without Using the Nose," Landfall, April, p. 19 (2000), http://www.titech-coop.or.jp/landfall/pdf/39/39-5moriizuminakamotoken.pdf.

http://www.sice.jp/handbook/%E5%A4%9A%E6%AC%A1%E5%85%83%E3%82%BB%E3%83%B3%E3%82%B5 [retrieved from internet on Mar. 14, 2013], 3 pages.

http://www.shse.u-hyogo.ac.jp/kumagai/eac/ea/chromato.htm, [retrieved from internet on Mar. 14, 2013], 6 pages.

http://en.wikipedia.orq/wiki/Van_Deemter_equation [retrieved from internet on Mar. 14, 2013], 4 pages.

http://www.qls.co.jp/technique/technique_data/basics_of_gc/p1_3.html [retrieved from internet on Mar. 14, 2013] 4 pages.

* cited by examiner

ODOR SENSING SYSTEM

CROSS-REFERENCE TO RELATED APPLICATIONS

This application is the U.S. National Phase under 35 U.S.C. §371 of International Application No. PCT/JP2012/007568, filed Nov. 26, 2012, the contents of which are herein incorporated by reference in its entirety.

BACKGROUND

Typically, an odor is recognized as a result of intricately combined information associated with different kinds of odor molecules. Therefore, it is extremely difficult to identify an odor by measuring the amount of a single kind of odor molecule. Higher animals recognize an odor through the following mechanism. First, olfactory receptors (approximately ten million olfactory cells), which are present on the olfactory epithelium in the depth of the nasal cavity, recognize individual odor molecules. Then, detection signals of the odor molecules from the olfactory receptors are input, in the form of electrical pulses, to the olfactory bulb located in front of the cerebrum via electrical wires called axons. Finally, the detection signals are transformed into a two-dimensional image represented by an ignition pattern of glomeruli present on the surface of the olfactory bulb.

One type of conventional odor sensing system is configured to have a plurality of odor sensors to identify odor molecules by simulating the above explained odor recognition mechanism of higher animals. In such a conventional odor sensing system, the detection accuracy strongly depends on the number of odor sensors. However, a large number of such odor sensors limits downsizing of the odor sensing system. Due to this, a small odor sensing system capable of detecting a variety of odors with sufficiently high accuracy has not been developed as of yet. Considering the steady expansion in the need for on-the-spot odor sensing, the development of a small, high accuracy odor sensing system is desired.

SUMMARY

In accordance with one embodiment, an odor sensing system is provided. The odor sensing system comprises a plurality of odor sensors configured to output a detection signal in response to at least one odor molecule, at least one chromatographic membrane disposed at the plurality of odor sensors through which the odor molecule diffuses to reach the odor sensor, and a pattern analyzer configured to analyze the detection signals over time to identify the odor molecule.

In accordance with another embodiment, an odor sensing method is provided. The odor sensing method comprises a plurality of odor sensors, each odor sensor being configured to output a detection signal in response to at least one odor molecule, at least one chromatographic membrane disposed at the plurality of odor sensors through which the odor molecule diffuses to reach the odor sensor, and a pattern analyzer configured to analyze the detection signals over time to identify the odor molecule, exposing a sample to the odor sensing system, where the sample comprises at least one odor molecule, and analyzing the detection signals over time.

In accordance with yet another embodiment, a method of manufacturing an odor sensing system is provided. The method comprises providing a plurality of odor sensors, each odor sensor being configured to output a detection signal in response to at least one odor molecule, providing at least one chromatographic membrane disposed at the plurality of odor sensors through which the odor molecule diffuses to reach the odor sensor, and programming a pattern analyzer to analyze detection signals over time to identify the odor molecule.

DETAILED DESCRIPTION

Figure 1:
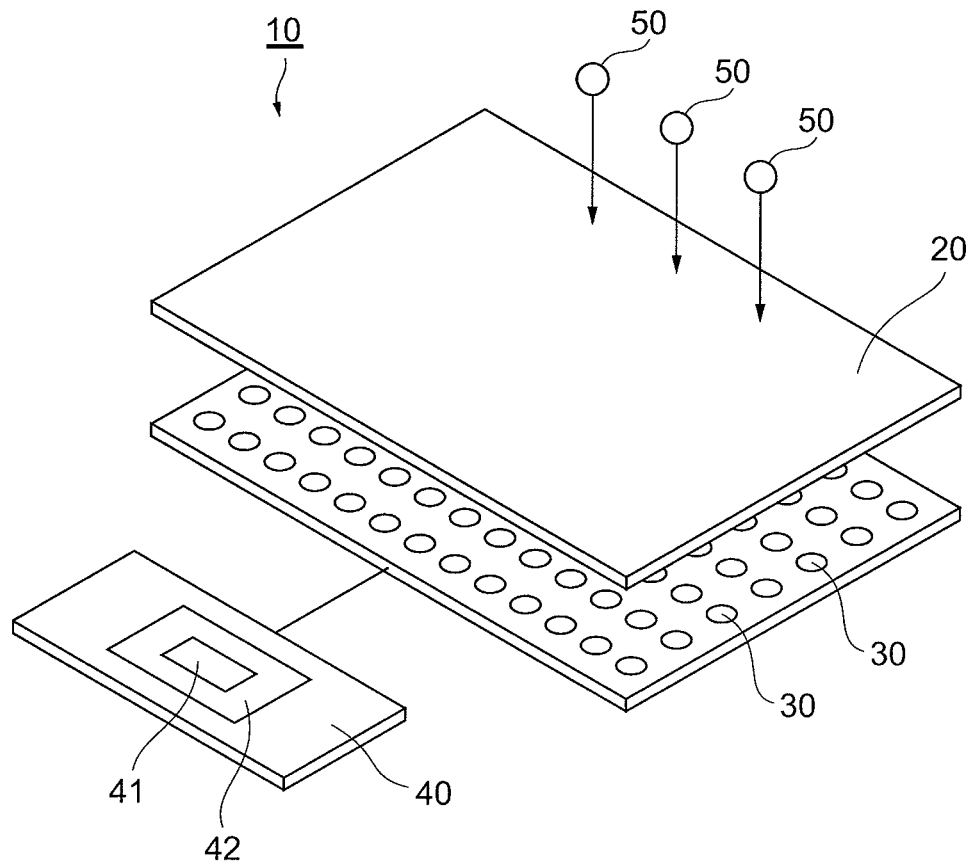
FIG. 1 shows an odor sensing system in accordance with an embodiment of the present disclosure.

In the following detailed description, reference is made to the accompanying drawings, which form a part hereof. In the drawings, similar symbols typically identify similar components, unless context dictates otherwise. Further, the drawings are intended to be explanatory and may not be drawn to scale. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

FIG. 1 shows an odor sensing system 10 in accordance with an embodiment of the present disclosure. The odor sensing system 10 may be provided with a plurality of odor sensors 30, each odor sensor 30 being configured to output a detection signal in response to at least one odor molecule 50; at least one chromatographic membrane 20 disposed at the plurality of odor sensors 30, through which the odor molecule 50 diffuses to reach the odor sensor 30; and a pattern analyzer 40 configured to analyze the detection signals over time so as to identify the odor molecule 50. The detection signals are transferred from the odor sensors 30 to the pattern analyzer 40. The pattern analyzer 40 may be configured to store data 41 of changes in the detection signals over time. The plurality of odor sensors 30 may be configured to individually detect a different odor molecule 50.

Figure 2:
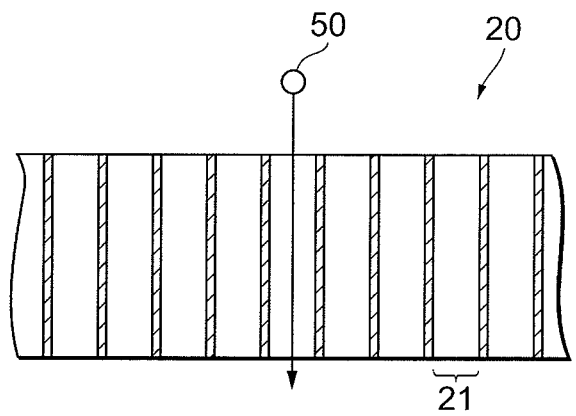
FIG. 2 shows a cross-sectional view of a chromatographic membrane in accordance with an embodiment of the present disclosure.

FIG. 2 shows a cross-sectional view of the chromatographic membrane 20 in accordance with an embodiment of the present disclosure. The chromatographic membrane 20 may have a plurality of pores 21 through which the odor molecule 50 diffuses to reach the odor sensor 30. For example, the chromatographic membrane 20 may be a microporous membrane having a plurality of penetrating pores configured to allow natural diffusion of the odor molecules 50. The microporous membranes may be made, for example, from a polymer material, a metal material, a ceramic material, or a glass material. A diameter of the pore 21 and a thickness of the chromatographic membrane 20 may be selected so as not to disturb the natural diffusion of the odor molecules 50 in a gaseous state. For example, the diameter of the pore 21 may be from about 1 nanometer to about 10 micrometers. The thickness of the chromatographic membrane 20 may be from about 1 micrometer to about 10 millimeters. The pores 21 may be formed, for example, by self-organization through phase separation, nanofiber integration, or laser machining. The chromatographic membrane 20 may be replaced with a new chromatographic membrane 20 periodically or for every odor detection, as desired. Replacement of the membrane between samples reduces or eliminates the risk of contamination.

Figure 3:
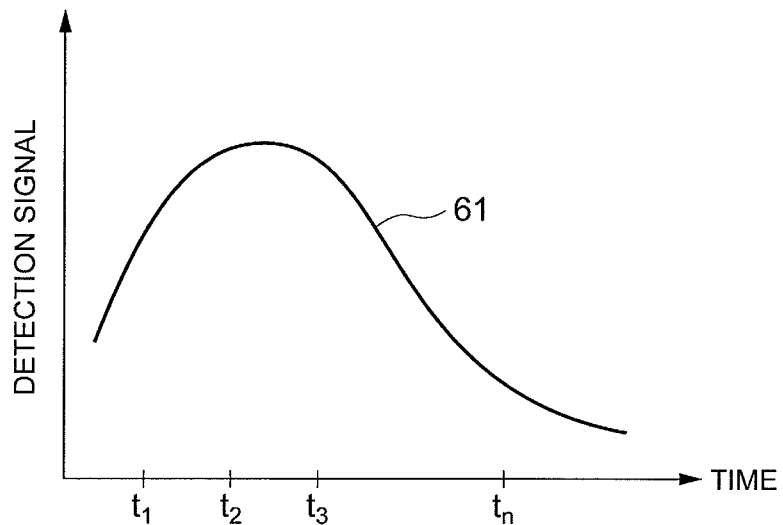
FIG. 3 shows a change in a detection signal over time in accordance with an embodiment of the present disclosure.

FIG. 3 shows a change in a detection signal 61 over time in accordance with an embodiment of the present disclosure. The odor sensors 30 output the detection signal 61 in response to the odor molecule 50. Here, the detection signal 61 changes over time and the change depends on the behavior of the odor molecule 50 when the odor molecule 50 is going through the pore 21 toward the odor sensor 30. Depending on the affinity between the odor molecule 50 and a chemical property of the pore 21, the manner in which the odor molecule 50 diffuses through the pore 21 toward the odor sensor 30 may be changed. For example, in one aspect, a diffusion velocity of the odor molecule 50 may depend on the affinity between the odor molecule 50 and the chemical property of the pore 21. In another aspect, a change in the number over time of odor molecules 50 diffused through the chromatographic membrane 20 per unit time may depend on the affinity between the odor molecules 50 and the chemical property of the pore 21. In a further aspect, a change in a ratio over time of the number between two different kinds of odor molecules 50 diffused through the chromatographic membrane 20 per unit time may depend on a difference in the affinity between the two different kinds of odor molecules 50 with respect to the chemical property of the pores 21.

Figure 4:
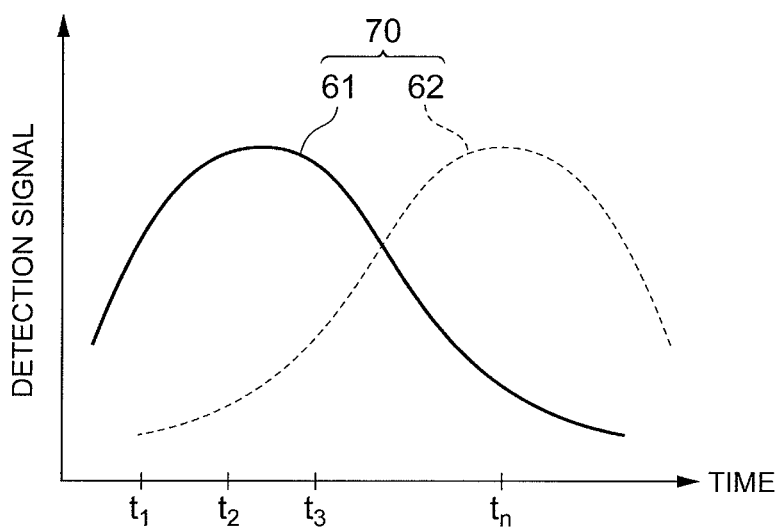
FIG. 4 shows a change in detection signals over time in accordance with an embodiment of the present disclosure.

For example, as shown in FIG. 4, the detection signals 61 and 62 are those output from the odor sensors 30 in response to two different kinds of odor molecules 50. The difference between the detection signals 61 and 62 may depend on a difference in the affinity between the two different kinds of odor molecules 50 with respect to the same chemical property of the pores 21. Consequently, not only the combination of the plurality of detection signals at one point in time, but also the changes in one or more of the detection signals at respective time points (t1, t2, . . . , tn) can be used to identify one or more kinds of the odor molecules 50. The change in the detection signal 61 over time may be discretely sampled at respective time points (t1, t2, . . . , tn) to create the data 41. The pattern analyzer 40 may detect the change in the detection signal 61 and continuously conduct multivariate analysis or pattern recognition to compare the change in the detection signal 61 with the data 41 of the sampled detection signal 61 so as to identify the odor molecule 50 with sufficiently high accuracy, even with a small number of the odor sensors 30. The data 41 of the sampled detection signal 61 may be associated with the chemical property of the pore 21 through which the odor molecule 50 diffuses. The pattern analyzer 40 may have a database 42 of the detection signals correlated with known odor molecules 50.

As a further example, as shown in FIG. 4, the detection signals 61 and 62 may be combined into a composite signal 70. The change in the composite signal 70 over time may be discretely sampled at respective time points (t1, t2, . . . , tn) to create the data 41. The pattern analyzer 40 may detect the change in the composite signal 70 and continuously conduct multivariate analysis or pattern recognition to compare the change in the composite signal 70 with the data 41 of the sampled composite signal 70 so as to identify the two different kinds of odor molecules 50 with sufficiently high accuracy, even with a small number of the odor sensors 30. The data 41 of the sampled composite signal 70 may be associated with the chemical property of the pores 21 through which the two different kinds of odor molecules 50 diffuse. The pattern analyzer 40 may have a database 42 of the composite signals correlated with known odor molecules 50.

Figure 5:
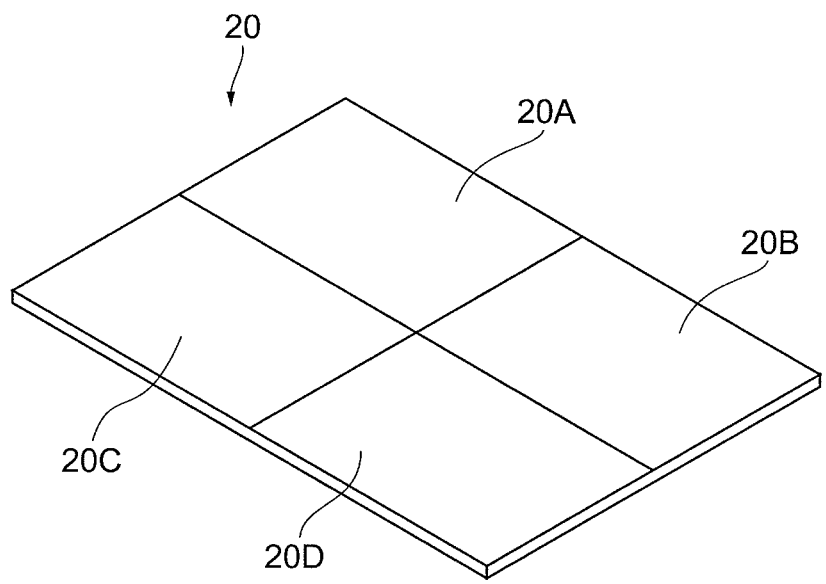
FIG. 5 shows a schematic view of a plurality of chromatographic membranes in accordance with an embodiment of the present disclosure.
Figure 6:
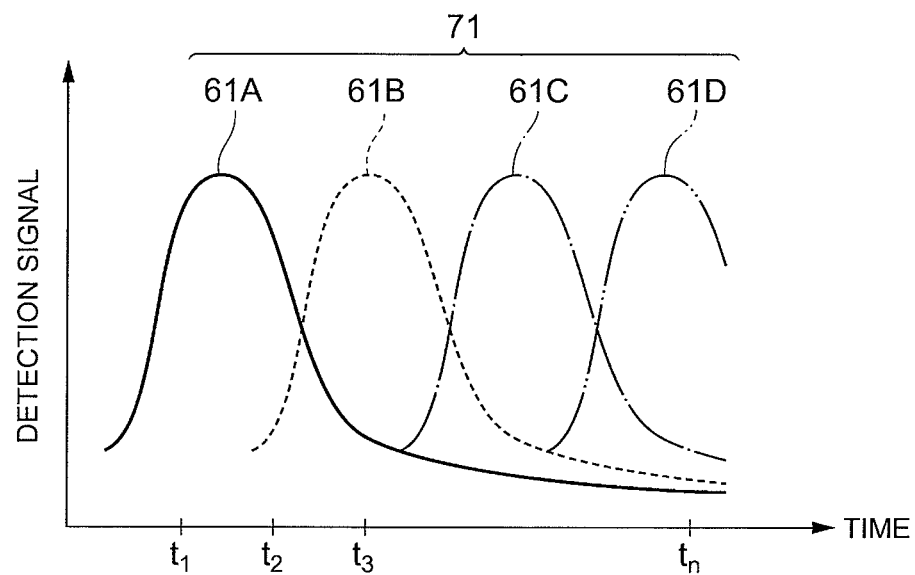
FIG. 6 shows a change in detection signals over time in accordance with an embodiment of the present disclosure.

As shown in FIG. 5, the at least one chromatographic membrane 20 may be provided with a plurality of chromatographic membranes 20A, 20B, 20C, and 20D. In one non-limiting aspect of the present disclosure, at least two of the plurality of chromatographic membranes 20A, 20B, 20C, and 20D may have different chemical properties from one another. As shown in FIG. 6, the detection signals 61A, 61B, 61C, and 61D are those output from the odor sensors 30 in response to the same kind of odor molecules 50. Depending on a difference in the affinity among the chromatographic matographic membranes 20A, 20B, 20C, and 20D with respect to the same kind of odor molecules 50, the manner in which the same kind of odor molecules 50 diffuse through the pore 21 toward the odor sensors 30 may be changed. The chemical properties of the chromatographic membranes 20A, 20B, 20C, and 20D may be acidity, basicity, hydrophilicity, and hydrophobicity, respectively. Other chemical or biological properties may be used individually or in combination for the various chromatographic membranes.

The detection signals 61A, 61B, 61C, and 61D may be combined into a composite signal 71. The change in the composite signal 71 over time may be discretely sampled at respective time points (t1, t2, ..., tn) or continuously to create the data 41. The pattern analyzer 40 may detect the change in the composite signal 71 and continuously conduct multivariate analysis or pattern recognition to compare the change in the composite signal 71 with the data 41 of the sampled composite signal 71 so as to identify the same kind of odor molecules 50 with sufficiently high accuracy, even with a small number of the odor sensors 30. The data 41 of the sampled composite signal 71 may be associated with the chemical properties of the chromatographic membranes 20A, 20B, 20C, and 20D through which the same kind of odor molecules 50 diffuse. The composite signal 71, whose data amount is four times greater than the respective detection signals 61A, 61B, 61C, and 61D, allows highly accurate odor sensing.

Alternatively, instead of preparing the plurality of chromatographic membranes 20A, 20B, 20C, and 20D with each having different chemical properties from one another, different surface treatments may be applied to different surface areas of the one chromatographic membrane 20 so that each of the different surface areas may have different chemical properties from one another.

Alternatively, the plurality of chromatographic membranes 20A, 20B, 20C, and 20D may have the same chemical property instead of different chemical properties.

The odor sensor 30 may be a commercially available sensor used for odor sensing, such as a ceramic semiconductor sensor, a quartz resonator sensor, a conductive polymer sensor, a bulk acoustic wave sensor, a surface acoustic wave sensor, an acoustic plate mode sensor, or an infrared absorption sensor. In one aspect, at least two of the plurality of odor sensors 30 may be configured to output different detection signals in response to the same odor molecule so that a combination of the detection signals can be used to identify the odor molecule 50. The plurality of odor sensors 30 may be arranged, for example, in a 2-dimensional grid pattern, specifically in two mutually perpendicular directions. For example, in the case where the plurality of odor sensors 30 are arranged in an array of 10 rows and 10 columns, it may be possible to form the plurality of odor sensors 30 having an entire size of a few square millimeters to a few square centimeters.

The pattern analyzer 40 may be a computer having an arithmetic processor and a memory programmed to analyze the detection signals over time so as to identify the odor molecule 50.

The manner in which the chromatographic membrane 20 separates the odor molecules 50 based on the principles of chromatography will be explained below. Chromatography can be considered as continuously performing countercurrent distribution (which is applied to separation of substances having close distribution ratios) to separate substances. With a distribution ratio D, the amount p of solute in the upper layer and the amount Y of solute in the lower layer upon reaching equilibrium can be expressed as:

[Math. 1]

$$P = \frac{D}{1+D} \tag{1}$$

[Math. 2]

$$Y = \frac{1}{1+D} \tag{2}$$

Here, Y=1−p, and expressing this equation in terms of the distribution ratio D by using the binomial theorem yields:

[Math. 3]

$$\left(\frac{D}{1+D} + \frac{1}{1+D}\right)^n = 1 \tag{3}$$

The portion $T_{n,r}$ in the r-th tube after n transfers can be expressed as:

[Math. 4]

$$\frac{n!}{r!(n-r)!}\left(\frac{D}{1+D}\right)^n D^r = \frac{n!}{r!(n-r)!} P^r (1-P)^{r-2} \tag{4}$$

Figure 7:
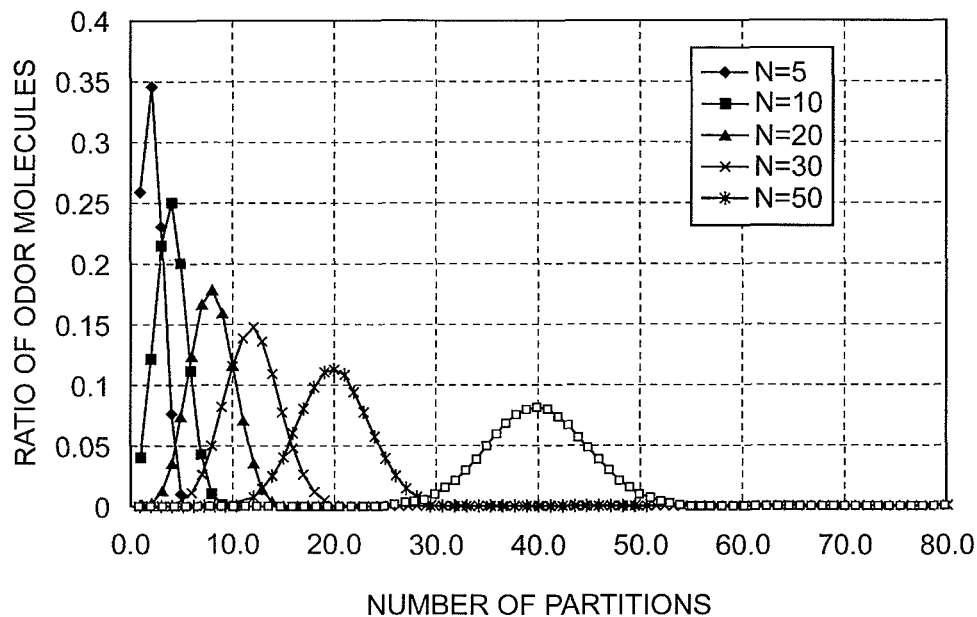
FIG. 7 shows the number of partitions and the distribution ratio of the odor molecules in the mobile phase with different numbers of plates (with the distribution ratio being 0.5, and N denoting the number of theoretical plates) in accordance with an embodiment of the present disclosure.
Figure 8:
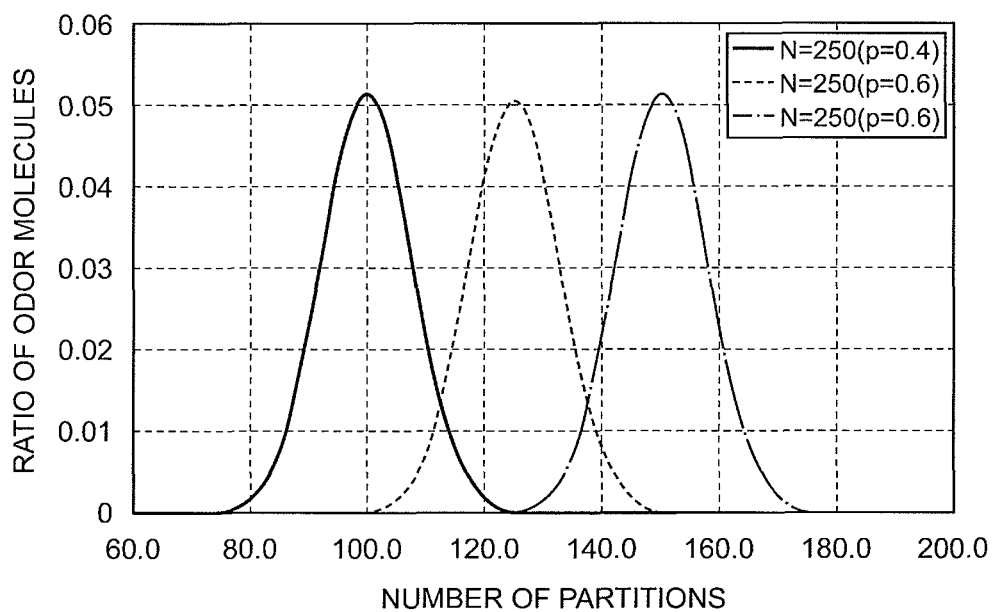
FIG. 8 shows the number of partitions and the distribution ratio of the odor molecules in the mobile phase (with the number of theoretical plates being N=250) in accordance with an embodiment of the present disclosure.

FIG. 7 shows a graph of the distribution ratio of the odor molecules in the mobile phase according to equation (4) in the case where n transfers are performed with a distribution ratio of 0.5. FIG. 8 shows a graph of the distribution ratio of the odor molecules in the mobile phase in cases where the number of partitions n is 250 and the distribution ratio is 0.4, 0.5, and 0.6, respectively.

Figure 9:
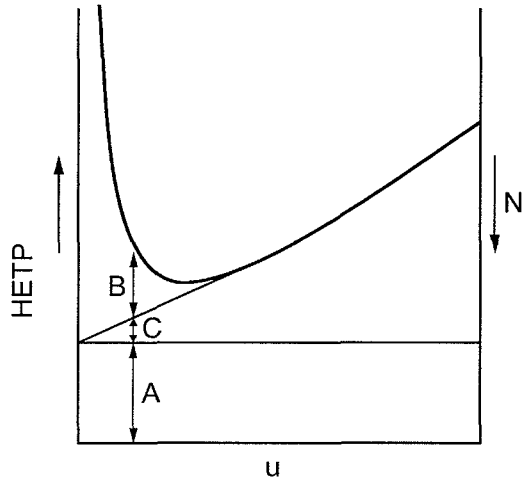
FIG. 9 shows a height equivalent to a theoretical plate (the Van Deemter equation) in accordance with an embodiment of the present disclosure.

In chromatography, the horizontal axis is considered to represent progress in time. The odor molecules 50 having different adsorption properties (having different distribution ratios) can be separated in time as shown in FIGS. 7 and 8. The composition ratio of the odor molecules 50 having different distribution ratios varies from time to time. The separation of the odor molecules 50 becomes easy with a combination having a large difference between their distribution ratios (i.e., the affinity between the odor molecule 50 and the pore 21). By combining pores 21 having different chemical properties, even if the separation of the odor molecules 50 is incomplete, the odor sensing system in the present disclosure can be applicable as long as the changes in the detection signals over time is detected. Precision of the identification improves as the separation efficiency improves in the separation by use of the chromatographic membrane 20. Considering the efficiency in terms of the column efficiency in chromatography, the efficiency can be evaluated in terms of the number of theoretical plates N (or the height equivalent to a theoretical plate: HETP). FIG. 9 shows a height equivalent to a theoretical plate (the Van Deemter equation).

[Math. 5]

$$N = \left(\frac{t_R}{q_t}\right)^2 \tag{5}$$

[Math. 6]

$$H = \frac{L}{N} \tag{6}$$

[Math. 7]

$$H = A + \frac{B}{u} + Cu \tag{7}$$

Where:
$t_R$ denotes progress in time;
L denotes a column length;
$2q_r$ denotes a peak standard deviation;
H denotes a height equivalent to a theoretical plate;
N denotes the number of theoretical plates;
A denotes a multipath diffusion;
B denotes a molecular diffusion;
C denotes a non-equilibrium diffusion of odor molecule transfer in the liquid phase/gas phase; and
U denotes an average flow speed of carrier gas.

According to equation (7), in order to improve the separation efficiency (decrease HETP), reducing the multipath diffusion (A), the molecular diffusion (B), and the non-equilibrium diffusion of odor molecule transfer in the liquid phase/gas phase (C) is effective. Since the present disclosure assumes natural diffusion, it can be considered that the carrier gas speed (u) is constant. In order to decrease the multipath diffusion (A), it is desired that penetrating pores having no branches are provided.

Furthermore, in order to satisfy both the detection sensitivity and the separation efficiency, it is desired that a large number of penetrating pores, having a size smaller than the size of each odor sensor 30, be provided on top of the sensors 30. In the case where a microporous membrane (in which horizontal diffusion may occur) is used as the chromatographic membrane 20, it is desired that the diameter of the pore 21 be small.

The molecular diffusion (B) can be considered as being constant since it is determined by the diffusion coefficient of the odor molecule 50 in the carrier gas. As the molecular diffusion (B) decreases, HETP decreases and the separation efficiency improves. The non-equilibrium diffusion of odor molecule transfer in the liquid phase/gas phase (C) varies between the pore centers and the pore surfaces, so it is desired that the diameter of the pore 21 be as small as possible.

By estimating HETP according to equation (8) or (12), it is possible to estimate the thickness (L) of the chromatographic membrane 20 required for separation (concentration distribution in the present disclosure). B, Cs, and Cm in equation (8) are calculated according to the formulae below, where Ds=Cg and Dm=Cl.

[Math. 8]

$$HETP = A + \frac{B}{u} + (C_s + C_m)u \quad (8)$$

[Math. 9]

$$B = 2Dg \quad (9)$$

[Math. 10]

$$Cg = \frac{r^2}{Dg} \times \frac{1 + qK + 11K^2}{24(1+K)^2} \quad (10)$$

[Math. 11]

$$Cl = \frac{d_f^2}{Dl} \times \frac{2K}{3(1+K)^2} \quad (11)$$

Where:
Cs denotes a mass transfer resistance in the stationary phase;
Cm denotes a mass transfer resistance in the mobile phase;
Dg denotes a diffusion coefficient of the odor molecule 50 in the carrier gas;
Dl denotes a diffusion coefficient of the odor molecule 50 in the liquid phase;
r denotes a radius of the capillary column;
df denotes a membrane thickness in the liquid phase; and
k denotes a distribution ratio (weight of the solute in the liquid phase/weight of the solute in the gas phase).

[Math. 12]

$$H = 2sdp + \frac{2GD_m}{v} + \frac{w(dp + dc)^2 v}{D_m} + \frac{Rd_f^2 v}{D_S} \quad (12)$$

Where:
H denotes a plate height;
s denotes a particle shape;
dp denotes a particle diameter;
G, w, and R are constants;
Dm denotes a diffusion coefficient of a mobile phase;
dc denotes a capillary diameter;
df denotes a film thickness; and
Ds denotes a diffusion coefficient of a stationary phase.

Here, the diffusion coefficient D12 (Dg or Dm above) can be expressed by equation (13):

[Math. 13]

$$D_{12} = \frac{3}{16}\left(2(3.14)KT\frac{M_1 M_2}{M_1 M_2}\right)^{\frac{1}{2}} \frac{1}{n(3.14)q_{12}^2 W_D} f_D \quad (13)$$

Where:
M1 and M2 denote molecular weights of first and second odor molecules;
N denotes the number of molecules in the mixture;
K denotes a Boltzmann coefficient (1.380*10$^{-23}$ J/K);
T denotes an absolute temperature;
$W_D$ denotes a collision integral in diffusion;
q12 denotes a molecule diameter (collision diameter) calculated according to the law of intermolecular forces; and
$f_D$ denotes a correction term of approximately 1.

When the ideal gas law holds and $f_D$=1, equation (14) holds:

[Math. 14]

$$D_{12} = 1.858 \times 10^{-3} T^{\frac{3}{2}} \frac{[(M_1 M_2)/M_1 M_2]^{\frac{1}{2}}}{P q_{12}^2 W_D} \quad (14)$$

Here, q12 and $W_D$ are given by equations (15), (16), (17) and (18):

[Math. 15]

$$q_{12} = \frac{q_1 + q_2}{2} \quad (15)$$

[Math. 16]

$$W_D = \frac{A}{T^{*B}} + \frac{C}{\exp DT^*} + \frac{E}{\exp FT^*} + \frac{G}{\exp HT^*} \quad (16)$$

[Math. 17]

$$T^* = \frac{KT}{a_{12}} \quad (17)$$

-continued

[Math. 18]

$$a_{12} = (a_1 a_2)^{\frac{1}{2}} \tag{18}$$

Where:
A is 1.06036;
B is 0.15610;
C is 0.19300;
D is 0.47635;
E is 1.03587;
F is 1.52996;
G is 1.76474; and
H is 3.89411.

The HETPs of the odor molecules 50 in the chromatographic membrane 20 can be calculated according to the above equations, and the number of theoretical plates N corresponding to the thickness of the chromatographic membrane 20 and changes in the pore diameter can be calculated according to equation (6). The separation status shown in FIGS. 7 and 8 can be estimated by using the values obtained by the above calculation and different distribution ratios corresponding to the variation in the type of chromatographic membrane 20.

Figure 10:
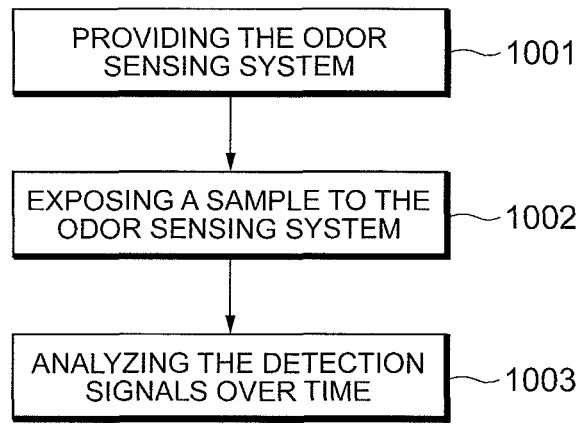
FIG. 10 is a flowchart showing an odor sensing method in accordance with an embodiment of the present disclosure.

FIG. 10 is a flowchart showing an odor sensing method. First, the odor sensing system 10 is provided (step 1001). Next, a sample is exposed to the odor sensing system 10 (step 1002). Here, the sample includes at least one odor molecule 50. Then, the detection signals are analyzed over time to identify the odor molecule 50 (step 1003). The analyzing step 1003 may be performed continuously. In one non-limiting aspect, the analyzing step 1003 may further include a step of detecting a change in one or more of the detection signals to identify the odor molecule 50 or a step of assembling the detection signals into a composite signal and then detecting a change in the composite signal to identify the odor molecule 50.

Figure 11:
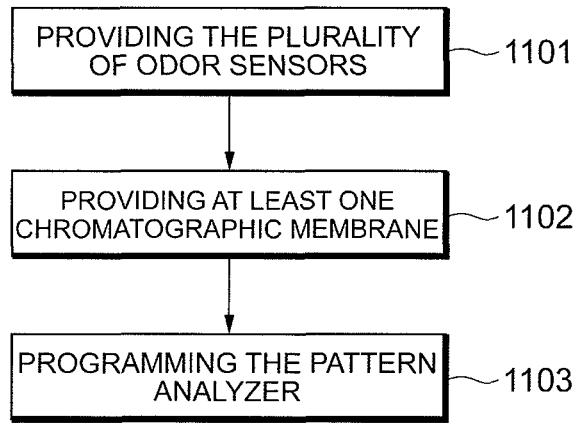
FIG. 11 is a flowchart showing a method of manufacturing an odor sensing system in accordance with an embodiment of the present disclosure.

FIG. 11 is a flowchart showing a method of manufacturing the odor sensing system 10. First, the plurality of odor sensors 30 are provided (step 1101). Next, at least one chromatographic membrane 20 is provided so as to be disposed at the plurality of odor sensors 30 through which the odor molecule 50 diffuses to reach the odor sensor 30 (step 1102). Then, the pattern analyzer 40 is programmed to analyze the detection signals over time to identify the odor molecule 50 (step 1103). The programming step 1103 may further include a step of programming the pattern analyzer 40 to detect changes in the detection signals.

EXAMPLES

Example 1

Calculating HETP and N for Different Odor Molecules

Figure 12:
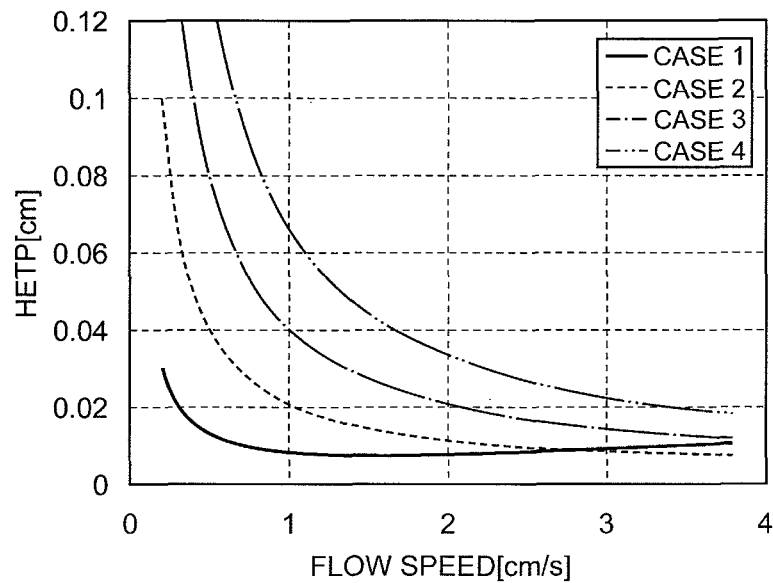
FIG. 12 shows a result of calculating a height equivalent to a theoretical plate for different odor molecules in accordance with an embodiment of the present disclosure.
Figure 13:
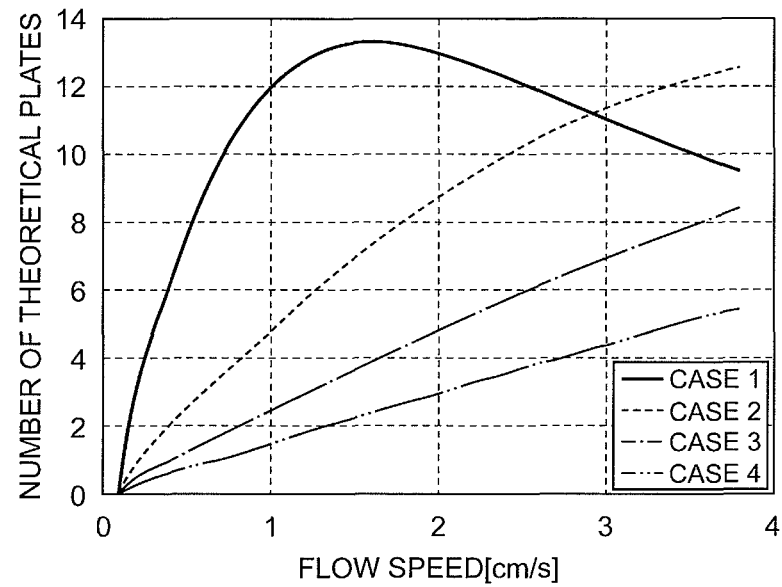
FIG. 13 shows a result of the number of theoretical plates for different odor molecules in accordance with an embodiment of the present disclosure.

The results of calculating the height equivalent to the theoretical plate (HETP) and the number of theoretical plates (N) for different kinds of odor molecules 50 with respect to the chromatographic membrane 20 having a thickness of 1 millimeter are shown in FIGS. 12 and 13. The calculation conditions are shown in Table 1. The results show that the chromatographic membrane 20 can effectively separate the different kinds of odor molecules 50 by optimizing the parameters below. The separation of the different kinds of odor molecules 50 makes it possible to differentiate how the odor molecule 50 diffuses through the chromatographic membrane 20 depending on the difference in the affinity among the different kinds of odor molecules 50 with respect to the chemical property of the chromatographic membrane 20.

TABLE 1

| Parameters | Case 1 | Case 2 | Case 3 | Case 4 |
| --- | --- | --- | --- | --- |
| Membrane thickness L (cm) | 0.1 | 0.1 | 0.1 | 0.1 |
| Diffusion coefficient Dg (cm²/s) | 0.03 | 0.1 | 0.2 | 0.33 |
| Radius r (cm) | 0.0125 | 0.0125 | 0.0125 | 0.0125 |
| Distribution ratio k | 100 | 100 | 100 | 100 |

Example 2

Sensing Odor Molecules

As samples of two different kinds of odor molecules 50, D-limonene (i.e., odor of lemon) expressed by chemical formula 1 and hexyl acetate (i.e., odor of apple) expressed by chemical formula 2, were selected.

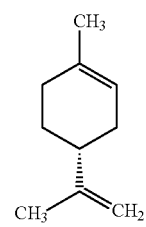

[Chem. 1]

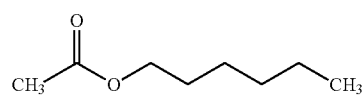

[Chem. 2]

As two chromatographic membranes 20 having different chemical properties from one another, an ultrafilter expressed by chemical formula 3 and a membrane filter expressed by chemical formula 4, were selected.

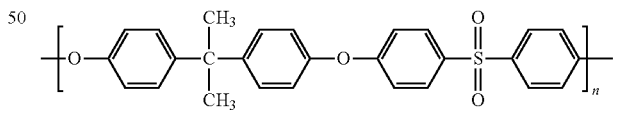

[Chem. 3]

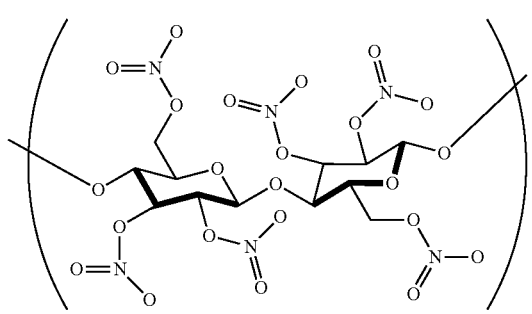

[Chem. 4]

-continued

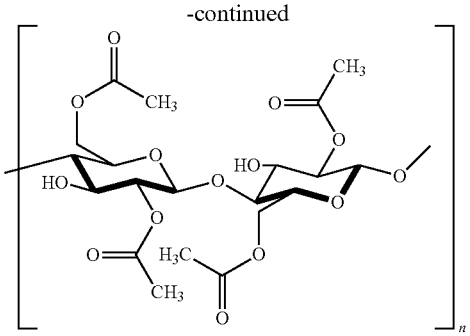

Figure 14:
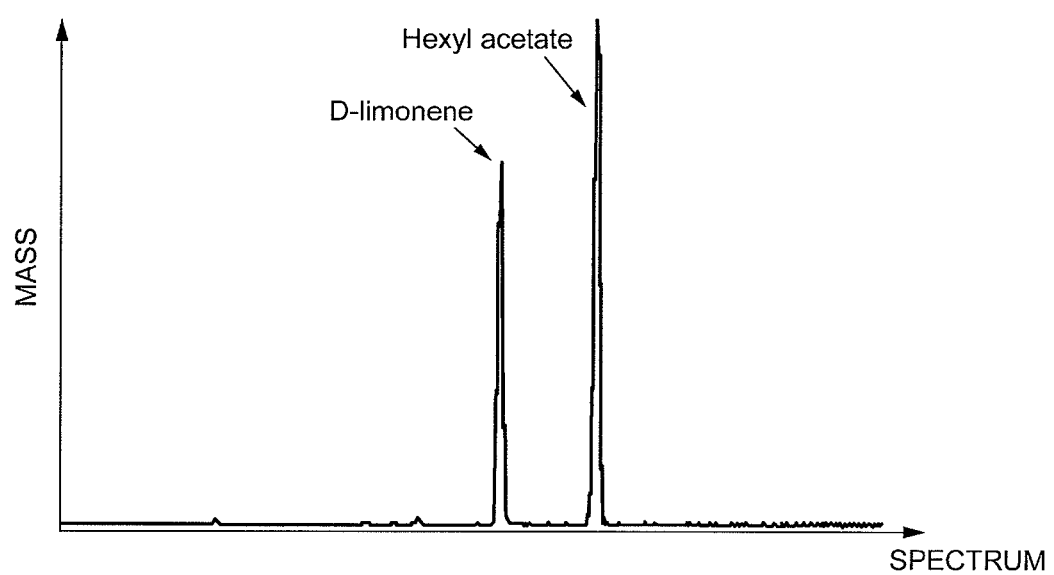
FIG. 14 shows a mass chromatogram of a mixed solution in accordance with an embodiment of the present disclosure.

The D-limonene was mixed with the hexyl acetate to prepare a mixed solution in such a manner that ratios of the D-limonene and the hexyl acetate to the mixed solution were both 50% by weight. After this, 0.1 grams of the mixed solution was poured into a 2 milliliter vial. Here, a chromatographic membrane was used for a septum. This vial was placed in a 15 milliliter vial and was left at a room temperature of about 23 degrees Celsius. Next, 0.1 milliliters of the internal gas within the vial was taken out at regular intervals, and the quantity ratio of the two different kinds of odor molecules 50 that diffused through the chromatographic membrane was calculated based on the area ratio of the GC/MS peaks. As a reference, FIG. 14 shows a mass chromatogram of the mixed solution.

Figure 15:
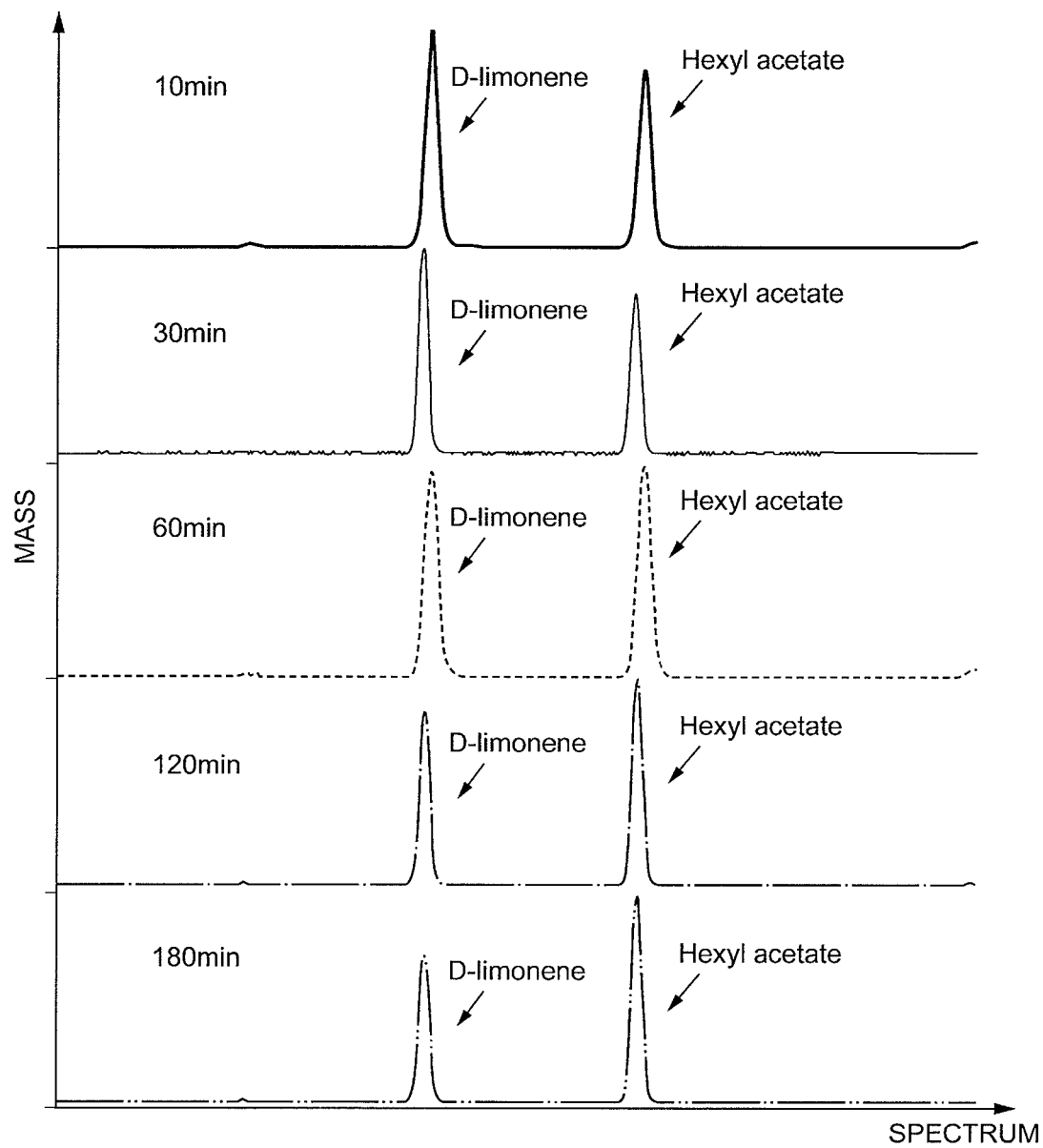
FIG. 15 shows temporal changes in a mass chromatograph of two different kinds of odor molecules using an ultrafilter as a chromatographic membrane in accordance with an embodiment of the present disclosure.
Figure 16:
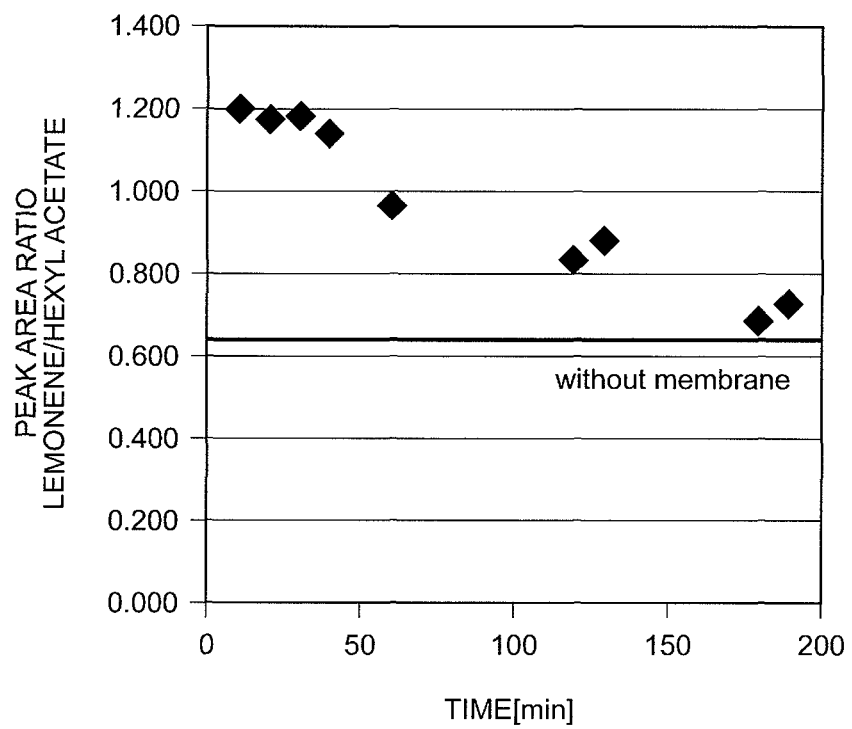
FIG. 16 shows temporal changes in a peak area ratio of two different kinds of odor molecules using an ultrafilter as a chromatographic membrane in accordance with an embodiment of the present disclosure.

FIG. 15 shows temporal changes in the mass chromatogram of the two different kinds of odor molecules 50 that diffused through the chromatographic membrane in the case where the ultrafilter was used as the chromatographic membrane 20. As a result of plotting temporal changes in the ratio of the D-limonene/hexyl acetate detected, as shown in FIG. 16, it was observed that the ratio of the D-limonene was higher at early stages but approached the reference ratio as time elapsed. The ultrafilter showed high permeability for the D-limonene. Table 2 shows temporal changes in the peak area ratio of the two different kinds of odor molecules 50, using the ultrafilter as the chromatographic membrane 20.

TABLE 2

| Time (minutes) | Peak area ratio of D-limonene/hexyl acetate |
|---|---|
| 10 | 1.201 |
| 20 | 1.179 |
| 30 | 1.185 |
| 40 | 1.138 |
| 60 | 0.958 |
| 120 | 0.830 |
| 130 | 0.878 |
| 180 | 0.685 |
| 190 | 0.725 |

Figure 17:
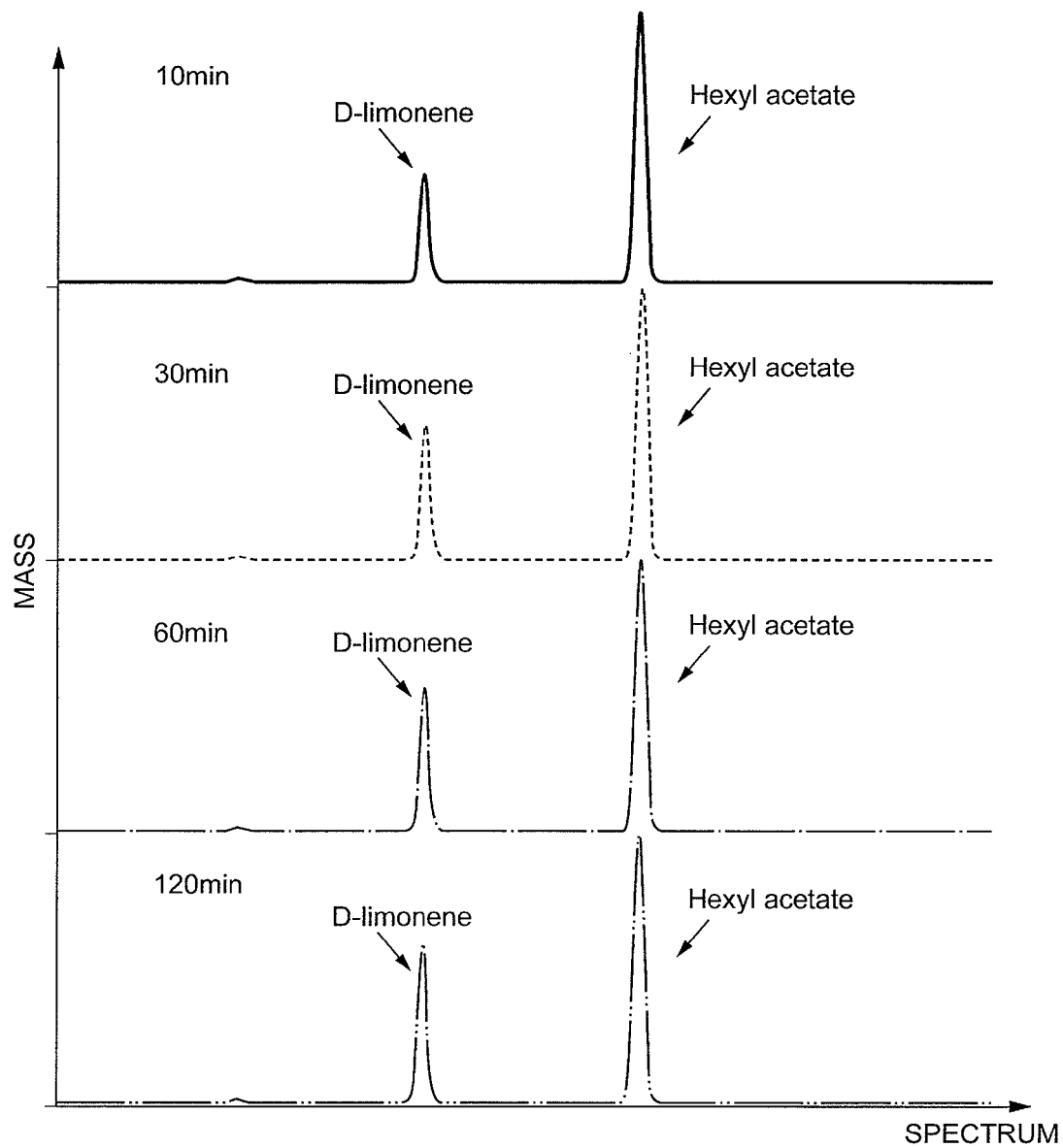
FIG. 17 shows temporal changes in a mass chromatograph of two different kinds of odor molecules using a membrane filter as a chromatographic membrane in accordance with an embodiment of the present disclosure.
Figure 18:
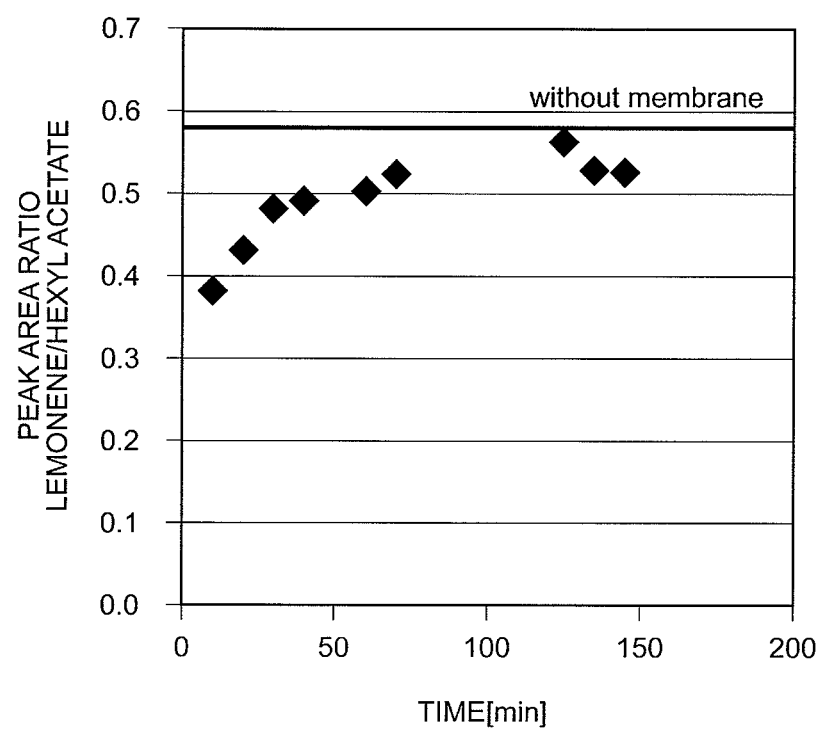
FIG. 18 shows temporal changes in a peak area ratio of two different kinds of odor molecules using a membrane filter as a chromatographic membrane in accordance with an embodiment of the present disclosure.

FIG. 17 shows temporal changes in the mass chromatogram of the two different kinds of odor molecules 50 that diffused through the chromatographic membrane in the case where the membrane filter was used as the chromatographic membrane 20. As a result of plotting temporal changes in the ratio of the D-limonene/hexyl acetate detected, as shown in FIG. 18, it was observed that the ratio of the hexyl acetate was higher at early stages but approached the reference ratio as time elapsed. The membrane filter showed high permeability for the hexyl acetate. Table 3 shows temporal changes in the peak area ratio of the two different kinds of odor molecules 50 using the membrane filter as the chromatographic membrane 20.

TABLE 3

| Time (minutes) | Peak area ratio of D-limonene/hexyl acetate |
|---|---|
| 10 | 0.382 |
| 20 | 0.429 |
| 30 | 0.478 |
| 40 | 0.490 |
| 60 | 0.502 |
| 70 | 0.522 |
| 125 | 0.564 |
| 135 | 0.527 |
| 145 | 0.525 |

Meanwhile, temporal changes in the ratio of the D-limonene/hexyl acetate were not observed with a glass filter sheet whose filtered particle diameter was about 0.6 micrometers, or a PTFE membrane filter whose pore size was about 0.1 micrometers.

The above explained results demonstrate that the same combination of the different kinds of odor molecules 50 exhibited different membrane permeation characteristics depending on the choice of the chromatographic membrane material and the pore diameter. Thus, it can be possible to obtain a detection signal that varies depending on the chemical property of the chromatographic membrane 20 and that varies over time by installing such a chromatographic membrane in front of the plurality of odor sensors 30. By providing the database 42 of such detection signals, it can be possible to sense an odor with accuracy.

While the present disclosure has been described with respect to a limited number of embodiments, a person skilled in the art, having the benefit of this disclosure, would appreciate that other embodiments can be devised which do not depart from the scope of the present disclosure as disclosed herein. Accordingly, the scope of the invention should be limited only by the attached claims.

The invention claimed is:

1. An odor sensing system comprising:
a plurality of odor sensors, each configured to output a detection signal in response to at least one odor molecule;
a plurality of chromatographic membranes, wherein the plurality of chromatographic membranes are identical to one another,
wherein at least one chromatographic membrane of the plurality of chromatographic membranes is disposed at the plurality of odor sensors through which the at least one odor molecule diffuses to reach the plurality of odor sensors; and
a pattern analyzer configured to analyze the detection signals over time to identify the at least one odor molecule.

2. The odor sensing system of claim 1, wherein the chromatographic membranes are microporous membranes.

3. The odor sensing system of claim 2, wherein the microporous membranes have a plurality of pores, and wherein at least two of the plurality of pores have different chemical properties from one another.

4. The odor sensing system of claim 3, wherein the chemical properties are selected from acidity, basicity, hydrophilicity, and hydrophobicity.

5. The odor sensing system of claim 1, wherein the pattern analyzer is configured to store data of changes in detection signals over time.

6. The odor sensing system of claim 5, wherein the data is associated with a chemical property of a pore of the plurality of chromatographic membranes through which the odor molecule diffuses.

7. The odor sensing system of claim 2, wherein the microporous membranes are configured to change a diffusion velocity of the odor molecule depending on an affinity between the odor molecule and the chemical property of the pore of the microporous membranes through which the odor molecule diffuses.

8. The odor sensing system of claim 2, wherein the microporous membranes are configured to change the number over time of odor molecules diffused through the microporous membrane per unit time depending on an affinity between the odor molecules and the chemical property of the pore of the microporous membranes through which the odor molecules diffuse.

9. The odor sensing system of claim 2, wherein the microporous membranes are configured to change a ratio over time of the number between two different kinds of odor molecules diffused through the microporous membranes per unit time depending on a difference in an affinity between the two different kinds of odor molecules with respect to the chemical property of pores of the microporous membranes through which the two different kinds of odor molecules diffuse.

10. The odor sensing system of claim 2, wherein a diameter of the pore of the microporous membranes is from about 1 nanometer to about 10 micrometers.

11. The odor sensing system of claim 2, wherein the microporous membranes are made from a polymer material, a metal material, a ceramic material, or a glass material.

12. The odor sensing system of claim 1, wherein the pattern analyzer is configured to detect changes in the detection signals.

13. The odor sensing system of claim 1, wherein the pattern analyzer is configured to conduct multivariate analysis to analyze the detection signals over time.

14. The odor sensing system of claim 1, wherein at least two of the plurality of odor sensors are configured to output different detection signals in response to the same odor molecule.

15. The odor sensing system of claim 1, wherein the plurality of odor sensors are arranged in two mutually perpendicular directions.

16. The odor sensing system of claim 1, wherein the plurality of odor sensors are arranged in a 2-dimensional grid pattern.

17. The odor sensing system of claim 1, wherein the pattern analyzer is configured to analyze the detection signals continuously.

18. The odor sensing system of claim 1, wherein the pattern analyzer is further configured to detect a change in one or more of the detection signals.

19. The odor sensing system of claim 1, wherein the pattern analyzer is further configured to assemble the detection signals into a composite signal.

20. The odor sensing system of claim 19, wherein the pattern analyzer is further configured to detect a change in the composite signal.

21. The odor sensing system of claim 19, further comprising a database of composite signals correlated with known molecules.

22. The odor sensing system of claim 1, further comprising a database of detection signals correlated with known molecules.

23. An odor sensing method comprising:
providing an odor sensing system comprising:
a plurality of odor sensors, each configured to output a detection signal in response to at least one odor molecule;
a plurality of chromatographic membranes, wherein the plurality of chromatographic membranes are identical to one another,
wherein at least one chromatographic membrane of the plurality of chromatographic membranes is disposed at the plurality of odor sensors through which the at least one odor molecule diffuses to reach the odor sensors; and
a pattern analyzer configured to analyze the detection signal over time to identify the at least one odor molecule;
exposing a sample to the odor sensing system, where the sample comprises the at least one odor molecule, by exposing the sample to the plurality of chromatographic membranes thereby causing the at least one odor molecule to diffuse through the at least one chromatographic membrane to reach the odor sensors; and
analyzing the detection signals over time.

24. The odor sensing method of claim 23, further comprising:
storing data of the detection signals over time.

25. The odor sensing method of claim 23, wherein the analyzing step is performed continuously.

26. The odor sensing method of claim 23, wherein the analyzing step further comprises detecting a change in one or more of the detection signals.

27. The odor sensing method of claim 23, wherein the analyzing step further comprises assembling the detection signals into a composite signal.

28. The odor sensing method of claim 27, wherein the analyzing step further comprises detecting a change in the composite signal.

29. The odor sensing method of claim 28, further comprising comparing the detection signals over time against a database to identify the odor molecule.

30. The odor sensing method of claim 28, further comprising comparing the change in the composite signal over time against a database to identify the odor molecule.

31. A method of manufacturing an odor sensing system, the method comprising:
providing a plurality of odor sensors configured to output a detection signal in response to at least one odor molecule;
providing a plurality of chromatographic membranes, wherein the plurality of chromatographic membranes are identical to one another,
wherein at least one of the plurality of chromatographic membranes is disposed at the plurality of odor sensors through which the at least one odor molecule diffuses to reach the at least one odor sensors; and
programming a pattern analyzer to analyze detection signals over time to identify the odor molecule.

32. The method of claim 31, further comprising:
applying different surface treatments to the at least one chromatographic membrane.

33. The method of claim 31, wherein the programming step further comprises programming the pattern analyzer to detect changes in the detection signals.

* * * * *

UNITED STATES PATENT AND TRADEMARK OFFICE
CERTIFICATE OF CORRECTION

PATENT NO. : 9,279,791 B2
APPLICATION NO. : 13/994094
DATED : March 8, 2016
INVENTOR(S) : Fukui et al.

Page 1 of 1

It is certified that error appears in the above-identified patent and that said Letters Patent is hereby corrected as shown below:

Specification

In Column 1, Line 7, delete "§371" and insert -- § 371 --, therefor.

In Column 4, Lines 55-56, delete "chromatographic matographic membranes" and insert -- chromatographic membranes --, therefor.

Signed and Sealed this
Fourteenth Day of June, 2016

Michelle K. Lee
*Director of the United States Patent and Trademark Office*